United States Patent
Lee et al.

(10) Patent No.: US 8,295,572 B2
(45) Date of Patent: Oct. 23, 2012

(54) DUAL-SPECTRUM HEAT PATTERN SEPARATION ALGORITHM FOR ASSESSING CHEMOTHERAPY TREATMENT RESPONSE AND EARLY DETECTION

(75) Inventors: Chia-Yen Lee, Taipei (TW); Si-Chen Lee, Taipei (TW); Wan-Jou Lee, Taipei (TW); Che-Wei Chang, Taipei (TW); Yu-Chun Chien, Taipei (TW); Chung-Ming Chen, Taipei (TW)

(73) Assignee: National Taiwan University, Taipei (TW)

( * ) Notice: Subject to any disclaimer, the term of this patent is extended or adjusted under 35 U.S.C. 154(b) by 195 days.

(21) Appl. No.: 12/965,642

(22) Filed: Dec. 10, 2010

(65) Prior Publication Data
US 2012/0148124 A1    Jun. 14, 2012

(51) Int. Cl.
G06K 9/00       (2006.01)
H01L 25/00     (2006.01)
(52) U.S. Cl. .................... 382/128; 382/274; 250/370.08
(58) Field of Classification Search .................. 382/100, 382/103, 106–107, 128, 129, 130, 131, 132, 382/133, 134, 162, 168, 173, 181, 199–201, 382/219–222, 232, 254, 274, 276, 295, 305, 382/312; 250/370.08, 353, 330; 600/473; 264/430
See application file for complete search history.

(56) References Cited

U.S. PATENT DOCUMENTS

| | | | | |
|---|---|---|---|---|
| 6,280,677 B1* | 8/2001 | Yakobson | ..................... | 264/430 |
| 2004/0119020 A1* | 6/2004 | Bodkin | ......................... | 250/353 |
| 2005/0285038 A1* | 12/2005 | Frangioni | ..................... | 250/330 |
| 2006/0097176 A1* | 5/2006 | Szu | ........................... | 250/370.08 |
| 2008/0260225 A1* | 10/2008 | Szu | ............................... | 382/128 |
| 2009/0318815 A1* | 12/2009 | Barnes et al. | ................. | 600/473 |

OTHER PUBLICATIONS

Szu et al., "Thermodynamic Free-Energy Minimization for Unsupervised Fusion of Dual-Color Infrared Breast Images", Proc. of SPIE vol. 6247, 62470P, (2006), 15 pages.
Ng et al., "Computerized Detection of Breast Cancer With Artificial Intelligence and Thermograms", Journal of Medical Engineering & Technology, vol. 26, No. 4, (Jul./Aug. 2002), pp. 152-157.
Lawson, "Implications of Surfce Temperatures in the Diagnosis of Breast Cancer", Clinical and Laoratory Notes, Canad. M.A.J. Aug. 15, 1956, vol. 75, pp. 309-310.
Zylberberg et al., "Initial Chemoimmunotherapy in Inflammatory Carcinoma of the Breast", American Cancer Society, vol. 49, Cancer Apr. 15, 1982, pp. 1537-1543.
Stark et al., "The Use of Thermovision in the Detection of Early Breast Cancer", Cancer Jun. 1974, vol. 33, pp. 1664-1670.
Lawson et al., "Breast Cancer and Body Temperature", Canad. Med. Ass. J. Jan. 12, 1963, vol. 88, pp. 68-70.

* cited by examiner

*Primary Examiner* — Seyed Azarian (57) ABSTRACT

Infra-red images of tumors carry the information of normal and cancerous tissues in every pixel. We developed a Dual-Spectrum Heat Pattern Separation (DS-HPS) algorithm to quantify the energy from the area of the high temperature tissues, called $q_H$ map, and decompose the body surface into the high and normal temperature areas based on a pair of middle-wave Infra-red images and long-wave Infra-red images. Further, with longitudinal registration, we can detect the cancerous tissues and assess the chemotherapy treatment response on a pixel by pixel basis according to the change of the $q_H$ map derived by the DS-HPS algorithm. The preliminary result shows the area and the $q_H$ values in the high temperature area are decreased as the patients receive more chemotherapy. These suggest the proposed algorithm could capture the incremental or decremental of the energies emitted by the cancerous tissues, which has the potentials for chemotherapy assessment and early detection.

19 Claims, 5 Drawing Sheets

DUAL-SPECTRUM HEAT PATTERN SEPARATION ALGORITHM FOR ASSESSING CHEMOTHERAPY TREATMENT RESPONSE AND EARLY DETECTION

FIELD OF THE INVENTION

The invention relates to a method for assessing chemotherapy treatment response and early detecting the tumors. More specifically, this invention relates to quantify the energy from high temperature tissues and decompose the body surface into the high and normal temperature area based on a pair of MIR (middle-wave Infra-red) and LIR (long-wave Infrared) images.

BACKGROUND OF THE INVENTION

Each year, about one million women are diagnosed with breast cancers in the world, which is the second leading cause of death for women. However, it can effectively improve the survival rate of patients by treating tumors at the early stage. Therefore, it is an important issue to detect the breast cancer early for the health of women.

Due to the advantages of non-invasion, non-contact, passivity, non-radiation and the ability of detecting the slight variations of temperature caused by neovascularization, Infrared imaging technique has been developed and employed for assessing chemotherapy treatment response. Serving as a medical imaging modality, the Infra-red (IR) image reveals the heat distribution on the surface of the human body. Cancerous tissues tend to have a higher temperature signature than their surrounding normal tissues, and for this reason, IR image has long been studied in hope to serve as an indicator for cancerous breast tissues. Nevertheless, the usefulness of IR images in detecting breast cancers remains controversial due to the physiological and environmental influence on the skin temperature distribution, and most importantly, there are no objective methods to quantitatively analyze lesion malignancy.

In the prior art, some methods have been reported to detect breast cancers or to assess treatment results of breast cancer chemotherapy using the IR image. These methods can be classified into two general categories, namely cross-sectional and longitudinal approaches. The cross-sectional approaches are mainly based on the comparison between the temperature of the normal area and that of the cancerous area of the breast. Although the breast area with tumors is expected to be higher than that of the normal breast area, it does not necessarily mean that the high temperature area in IR images corresponds to the tumor region (Lawson R., "Implications of surface temperatures in the diagnosis of breast cancer," Canadian Medical Association Journal, p. 309-310, 1956, Lawson R. N., Chughtai M. S., "Breast Cancer and Body Temperature," Canadian Medical Association Journal, p. 68-70, 1963 and Stark A. M., Way S., "The use of thermovision in the detection of early breast cancer," Cancer, p. 1664-1670, 1974). Therefore, it is too arbitrary to use the heat pattern acquired at a single time point as the basis to determine if there is a tumor in a breast.

Alternatively, the longitudinal approaches attempt to determine the malignancy of breast tissues based on the variation of heat pattern over several time points. The general idea is the heat pattern of each person remains roughly unchanged under similar physiological and environmental conditions. It has been observed that the heat patch in the IR image may shrink or even disappear in what seems like a direct correlation to the tumor blood vessels breaking down and eventually disappear as treatment progress (Zylberberg B., Salat-Baroux J., Ravina J. H., et al., "Initial chemoimmunotherapy in inflammatory carcinoma of the breast," Cancer, p. 1537-1543, 1982). However, a longitudinal approach may have the noisy variations caused by the physiological and environmental factors at different time points. Although the influence of such environmental variables as temperature, humidity, and so on, may be minimized through deliberate control, these factors could still disturb the IR intensity fluctuation and affects the quantitative estimation of IR intensity change along the time. To quantitatively analyze this subjective visual judgment on the change of a breast tumor, each breast is divided into four parts and compared with the temperature distribution of each pair of corresponding parts (Ng E. Y. K., Fok S. C., Peh Y. C., et al., "Computerized detection of breast cancer with artificial intelligence and thermograms," Journal of Medical Engineering & Technology, p. 152-157, 2002). The potential deficiency of this approach lies in the fallacious implicit assumption that the two breasts under the normal condition have the same temperature distributions.

In addition, prior to the present invention, the multiple-spectrum IR information is employed in a longitudinal approach at the same time in order to detect and quantify the breast cancer information collected under minimal physiological and environmental effects. By combining different energies received in the IR images of different spectrums, this approach offers an opportunity to further reduce the influence of the physiological and environmental factors. The blind source separation algorithm using two satellite-grade infrared cameras demonstrated that it is likely to detect breast cancer based on a pair of MIR and LIR breast images (Szu H., Miao L. and Qi H., "Thermodynamic free-energy minimization for unsupervised fusion of dual-color infrared breast images," SPIE, Florida, 2006). Since this algorithm mainly counts on the minute difference between the vectors, i.e., (MIR, LIR), of the cancerous and normal tissues, further investigation is required to attain a sufficient signal-to-noise ratio for this idea to be applied in a clinical setting.

According to the present invention, applicants have departed from the conventional wisdom, and had conceived and implemented a new longitudinal approach to estimate the heat pattern change on the breast skin with IR photon information from a pair of MIR and LIR cameras, rather than directly estimating the likelihood that each pixel contains cancerous tissue. The effects of chemotherapy on breast cancer are effectively traced and evaluated by using this method. The invention is briefly described as follows.

SUMMARY OF THE INVENTION

To minimize these effects of physiological and environmental factors effectively, the present invention provides a new and useful quantitative analysis method used to achieve the quantitative assessment of chemotherapy and detect the locations of tumors.

The quantitative analysis method of the present invention is to estimate the emitted energies of the high temperature area on the body surface from a pair of MIR and LIR cameras. A dual-spectrum heat pattern separation (DS-HPS) algorithm is developed to quantify the energy from high temperature tissues, denoted as a $q_H$ map, and decompose the body surface into the high and normal temperature area based on a pair of MIR and LIR images. Two descriptors are computed to indicate the structural and functional change of the tissues due to chemotherapy. One is the area of the high temperature region on the body surface and the other is the energies of high temperature tissues under the high temperature region.

Increasing or decreasing of these two descriptors may indicate the location of tumors and effectiveness of chemotherapy, respectively. Such an analysis method to quantify the energy map makes the invented algorithm extremely suitable for testing the human body applications including non-invasive detection of human body, assessing chemotherapy treatment response, early detection and etc.

In accordance with one aspect of the present invention, a quantitative analysis method is provided. The quantitative analysis method includes the following steps of:

(a) obtaining an energy reading vector of a corresponding point pair in an LIR image and an MIR image;

(b) establishing a cost function for the quantitative analysis method;

(c) deriving evolution equations; and (d) estimating an optimal $q_H$ map.

Preferably, the energy reading vector is the LIR and MIR energy emitted from an unit volume of a high and a normal temperature tissue, respectively;

Preferably, the $q_H$ map is the energy distribution of the high temperature tissue.

Preferably, the $q_H$ map could be used to distinguish a high temperature tissue from a normal temperature tissue.

The above aspects and advantages of the present invention will become more readily apparent to those ordinarily skilled in the art after reviewing the following detailed descriptions and accompanying drawings, in which:

BRIEF DESCRIPTION OF THE DRAWINGS

FIG. 5 shows the results of the DS-HPS algorithm of MIR and LIR images taken in a sequence of chemotherapy, wherein

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only it is not intended to be exhaustive or to be limited to the precise form disclosed.

Figure 1:
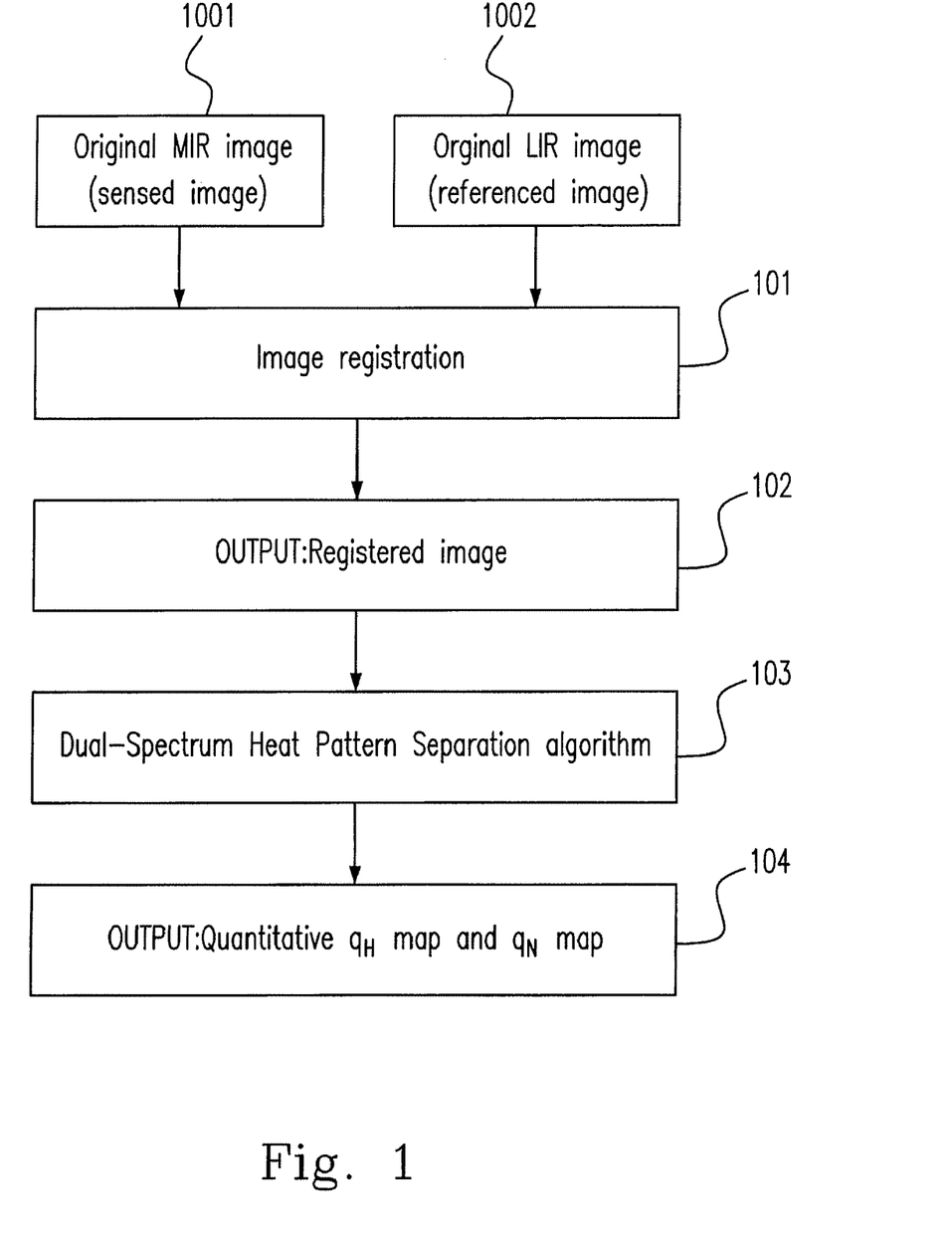
FIG. 1 shows that the software framework diagram of the present invention for obtaining energies distribution maps.

Please refer to FIG. 1, which shows a quantitative $q_H$ map being output in order to assess the chemotherapy response and detect the cancerous tissue through the present invention. As described in FIG. 1, the registration method 101 was used to obtain the registered image 102 in a MIR image 1001 and a LIR image 1002, and then DS-HPS algorithm 103 could obtain the quantitative $q_H$ and $q_N$ maps 104 to analyze the registered image 102. Preferably, the MIR image 1001 and the LIR image 1002 are obtained from a pair of MIR and LIR cameras. Preferably, the DS-HPS algorithm 103 uses a Blind Source Separation (BSS) concept to estimate the energy map ($q_H$ and $q_N$) of the high temperature area and the normal temperature area. As a result, the longitudinal variations of the area and the $q_H$ values in the high temperature area and its surrounding blood vessels could be computed from the quantitative $q_H$ map 104 to indicate the location of tumors and effectiveness of chemotherapy, since the cancerous tissues tend to have a higher temperature than the surrounding normal tissues.

Figure 2:
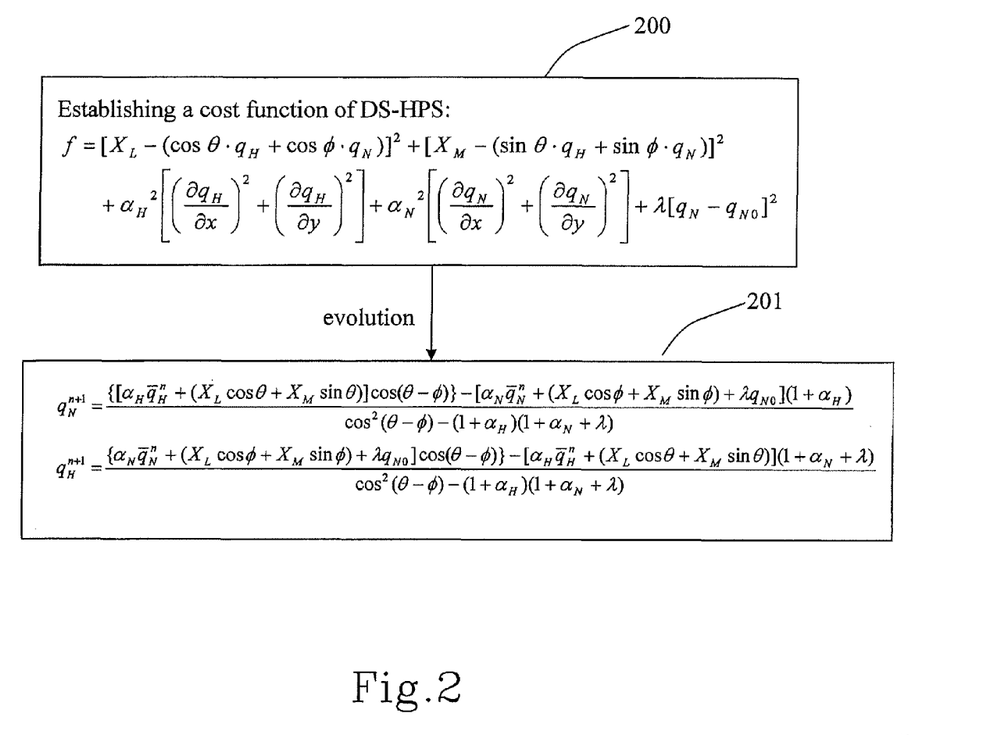
FIG. 2 contains evolution equations for a dual-spectrum heat pattern separation (DS-HPS) algorithm in the present invention.

Please refer to FIG. 2, which shows that the cost function and evolution equations of the DS-HPS algorithm in the present invention. The DS-HPS algorithm is formulated as a blind source separation (BSS) algorithm. Let $x=(x_L, x_M)$ be the energy reading vector of a corresponding point pair in the LIR and MIR images. Suppose $M_N$ and $M_N$ represents the MIR energy emitted from one unit volume of a normal and a high temperature tissue, respectively. Similarly, suppose $L_N$ and $L_H$ represents the LIR energy emitted from one unit volume of a normal and a high temperature tissue, respectively. Moreover, let $k_N$ and $k_H$ be the effective volume of the normal temperature tissue and the high temperature tissue, respectively. Note that the effective volume is not equivalent to the actual volume. The effective volume takes into account the energy attenuation during the propagation from the IR photon generation site to the breast surface. The energies detected by the LIR and MIR cameras may be approximated as a linear composition of the energies of the attenuated LIR and MIR photons originated from the high temperature and normal temperature tissues as follows:

$$\begin{bmatrix} x_L \\ x_M \end{bmatrix} = \begin{bmatrix} L_H & L_N \\ M_H & M_N \end{bmatrix} \begin{bmatrix} k_H \\ k_N \end{bmatrix} \quad (1)$$

If we let $L_H = A_H \cos\theta$, $M_H = A_H \sin\theta$, $L_N = A_N \cos\phi$ and $M_N = A_N \sin\phi$, equation (1) can be represented as:

$$\begin{bmatrix} x_L \\ x_M \end{bmatrix} = \begin{bmatrix} \cos\theta & \cos\phi \\ \sin\theta & \sin\phi \end{bmatrix} \begin{bmatrix} q_H \\ q_N \end{bmatrix} \quad (2)$$

where $q_H = A_H k_H$ and $q_N = A_N k_N$. $q_H$ and $q_N$ may be considered as the quantity approximately equivalent to the energies of the attenuated LIR and MIR photons originated from the high temperature tissue and the normal temperature tissue, respectively, and $\theta$ and $\phi$ are respectively the parameters of the high temperature and the normal temperature of the detected body region.

There are 4 unknowns in equation (2) but with only 2 equations. To solve this dilemma, it is assumed that the parameter $\phi$ and $q_N$ change slowly in the normal temperature region. Based on these two assumptions, the cost function 200 of this algorithm may be formulated as:

$$f = A + B + C + D + \lambda[q_N - q_{N0}]^2 \quad (3)$$

wherein $f = A + B + C + D + \lambda[q_N - q_{N0}]^2$, $A = [X_L - (\cos\theta \cdot q_H + \cos\phi \cdot q_N)]^2$, $B = [X_M - (\sin\theta \cdot q_H + \sin\phi \cdot q_N)]^2$, -continued
$$C = \alpha_H^2\left[\left(\frac{\partial q_H}{\partial x}\right)^2 + \left(\frac{\partial q_H}{\partial y}\right)^2\right],$$

$$D = \alpha_N^2\left[\left(\frac{\partial q_N}{\partial x}\right)^2 + \left(\frac{\partial q_N}{\partial y}\right)^2\right],$$

C and D are the smoothness constraint, $q_{N_0}$ represents the initial $q_N$ and $\lambda$ is the Lagrange multiplier.

The evolution equations for $q_N$ and $q_H$ may be derived as follows:

$$q_N^{n+1} = \frac{\{[\alpha_H \bar{q}_H^n + (X_L\cos\theta + X_M\sin\theta)]\cos(\theta - \phi)\} - [\alpha_N \bar{q}_N^n + (X_L\cos\phi + X_M\sin\phi) + \lambda q_{N_0}](1 + \alpha_H)}{\cos^2(\theta - \phi) - (1 + \alpha_H)(1 + \alpha_N + \lambda)} \quad (4)$$

$$q_H^{n+1} = \frac{\{\alpha_N \bar{q}_N^n + (X_L\cos\phi + X_M\sin\phi) + \lambda q_{N_0}]\cos(\theta - \phi)\} - [\alpha_H \bar{q}_H^n + (X_L\cos\theta + X_M\sin\theta)](1 + \alpha_N + \lambda)}{\cos^2(\theta - \phi) - (1 + \alpha_H)(1 + \alpha_N + \lambda)}$$

the $q_H$ map is thresholded in such a way that all values smaller than 0.001 are to 0. The high temperature region is then defined by the remaining nonzero pixels in the $q_H$ map.

Figure 3A:
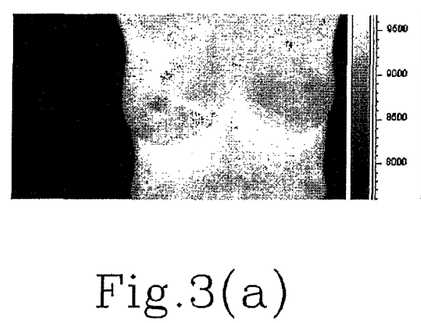
FIGS. 3(a) and (b) is a pair of original middle-wave Infrared (MIR) and long-wave Infra-red (LIR) images of a patient taken by MIR and LIR cameras, respectively.
Figure 3B:
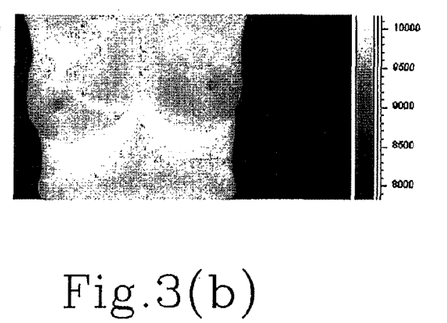

Please refer to FIGS. 3(a) and (b), which is a pair of original MIR and LIR images of a patient taken by MIR and LIR cameras, respectively. On the right side of each IR image there is a color reference gauge for pseudo-coloring.

Figure 4A:
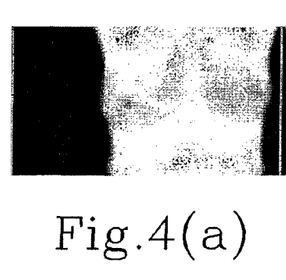
FIGS. 4(a) and (b) gives the MIR and LIR images, respectively, and FIG. 4(c) demonstrates the registered MIR image.
Figure 4B:
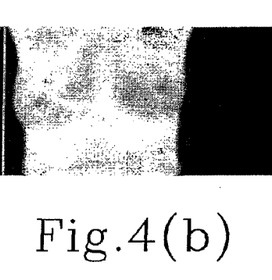
Figure 4C:
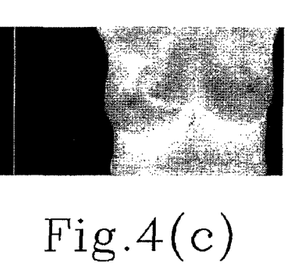

Please refer to FIG. 4, in which FIGS. 4(a) and (b) are the MIR and the LIR image, respectively, and FIG. 4(c) demonstrates the registered image via a registration method.

Figure 5A:
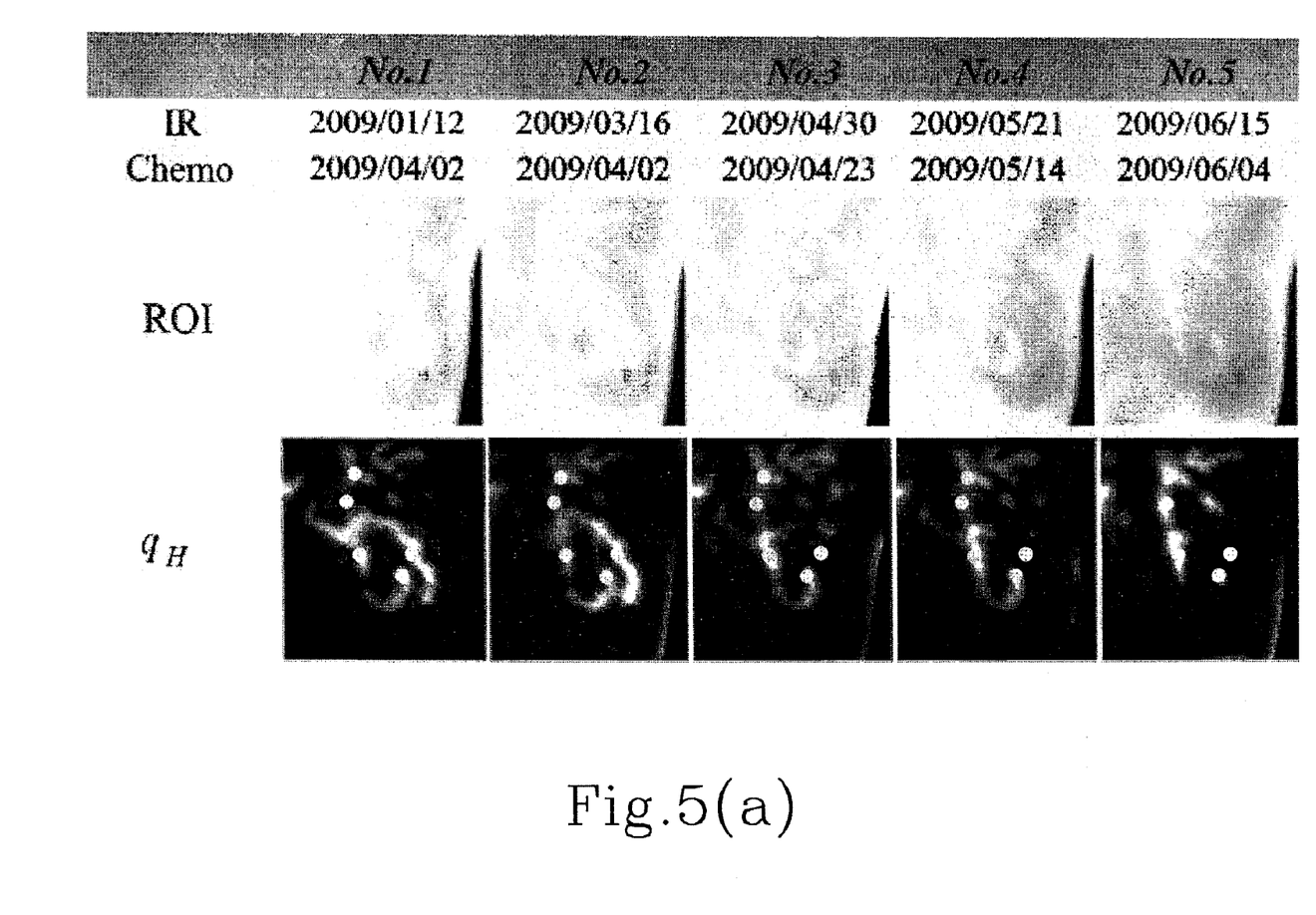
FIG. 5(a) is the results of the proposed approach for a sequence of chemotherapy.
Figure 5B:
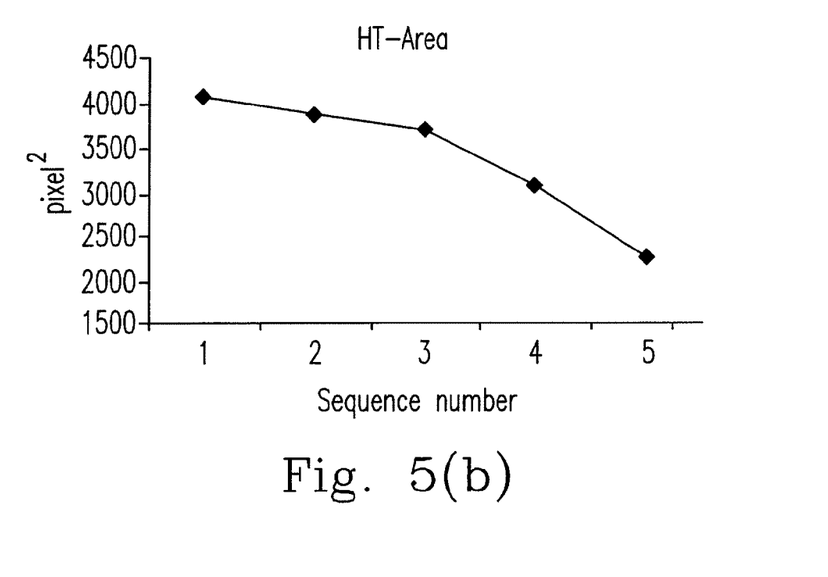
FIG. 5(b) represents the area of the high temperature region (HT-area) curve and FIG. 5(c) represents the energy originated from the high temperature tissues (HT-E) curves of five selected regions of interest (ROIs).
Figure 5C:
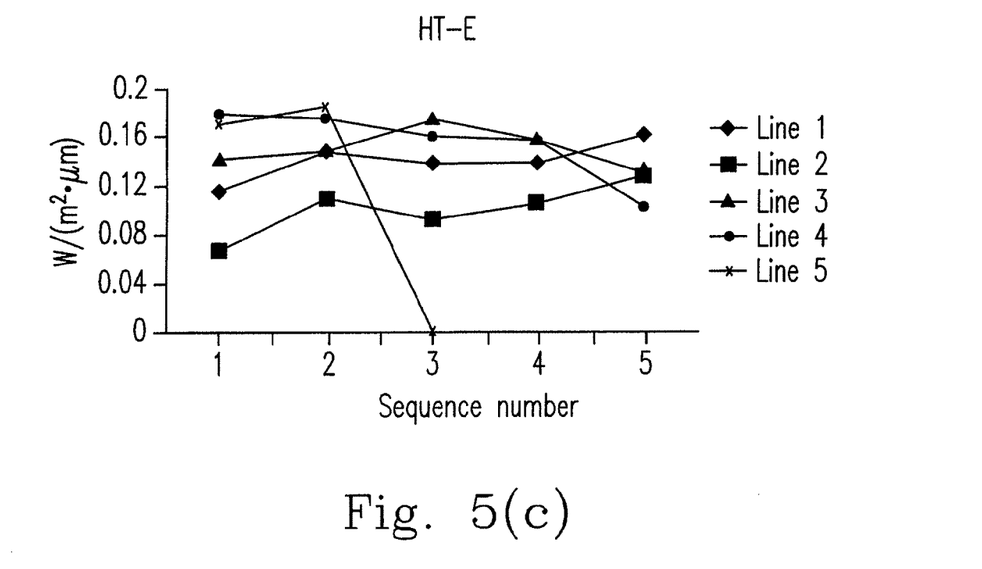

Please refer to FIG. 5, which presents the results of the DS-HPS algorithm for 5 pairs of MIR and LIR images taken in a sequence of chemotherapy. Two dates are shown on top of each column. The date on the row "IR" is the date when IR images were taken, and "chemo" is the chemotherapy day. Columns from top to bottom represent ROIs and $q_H$ maps respectively. If the effectiveness of the chemotherapy is assessed by observing only MIR or LIR images as shown in the ROI row of FIG. 5(a), it is obviously difficult to determine the change of the lesion size and its peripheral vessels quantitatively. In addition, we cannot estimate the variation of energy emitted from the cancerous tissues. However, the $q_H$ map in the last row of FIG. 5(a) clearly shows the structural change of cancerous tissues as well as the variation of energy detected from cancerous tissues. The two descriptors, i.e., HT-area and HT-E, are plotted in FIG. 5(b) and (c). HT-area shows a decreasing trend in the overall high temperature area, consistent with the reduced tumor size as confirmed by the MRI, Ultrasound and Mammogram. The tumor location is L11/4-12/3-1/4 (11:30 to 13:00 of the left breast, 3 to 4 cm from the nipple) and the tumor size is about 2 cm×4 cm. After chemotherapy, the tumor size becomes 0.9 cm×3 cm. Based on the HT-area result, five small ROIs are selected in each $q_H$ map for further estimate the probability of tumor in these locations and assess the response to chemotherapy. FIG. 5(c) shows the HT-E descriptor of five red areas. The HT-E curves of line 4 and line 5 show an obvious decreasing trend, consistent with the reduced tumor size as confirmed by the MRI result. It could be inferred that there might be tumors in the 4th and 5th locations of the infrared image due to energy decrease after chemotherapy. There is also a decreasing trend in HT-E curve of line 3 because the 3rd location is near the 4th location. The rising and oscillation of HT-E curves of line 1 and line 2 indicate the small probability of tumor in these locations.

In conclusion, the DS-HPS algorithm is proposed in the present invention for quantitative assessment of chemotherapy and early detection. The proposed DS-HPS algorithm identifies the high temperature region, as well estimates the energy of the attenuated LIR and MIR photons originated from the high temperature tissue and the normal temperature tissue, respectively. These two descriptors have been devised to quantify the change of the cancerous tissues, including the lesion size and peripheral vessel structures as well as the variation of the emitted energy. The result shows that the proposed approach has the potential for quantitative assessment of chemotherapy and indicating the locations of tumors.

Based on the above descriptions, it is understood that the present invention is indeed an industrially applicable, novel and obvious one with values in industrial development. While the invention has been described in terms of what are presently considered to be the most practical and preferred embodiment, it is to be understood that the invention should not be limited to the disclosed embodiment. On the contrary, it is intended to cover numerous modifications and variations included within the spirit and scope of the appended claims which are to be accorded with the broadest interpretation so as to encompass all such modifications and variations. Therefore, the above description and illustration should not be taken as limiting the scope of the present invention which is defined by the appended claims.

What is claimed is:

1. A quantitative analysis method for estimating energy distributions, comprising steps of:
obtaining an energy reading vector $X=(x_L, x_M)$ of a corresponding point pair in an long-wave Infra-red (LIR) image and a medium Infra-red (MIR) image respectively based on an equation (I):

$$\begin{bmatrix} x_L \\ x_M \end{bmatrix} = \begin{bmatrix} L_H & L_N \\ M_H & M_N \end{bmatrix}\begin{bmatrix} k_H \\ k_N \end{bmatrix},$$

wherein $(L_N, M_N)$ respectively represents the LIR and MIR energy emitted from an unit volume of normal temperature tissue, $(L_H, M_H)$ represents the LIR and MIR energy emitted from an unit volume of a high temperature tissue from an unit volume, and $k_H$ and $k_N$ are two effective volumes of the high temperature tissue and the normal temperature tissue respectively;

transforming the equation (I) into an equation (II), by letting $L_H=A_H\cos\theta$, $M_H=A_H\sin\theta$, $L_N=A_N\cos\phi$, $M_N=A_N\cos\phi$:

$$\begin{bmatrix} x_L \\ x_M \end{bmatrix} = \begin{bmatrix} \cos\theta & \cos\phi \\ \sin\theta & \sin\phi \end{bmatrix}\begin{bmatrix} q_H \\ q_N \end{bmatrix},$$

wherein $q_H=A_H k_H$, $q_N=A_N k_N$, and considering $q_H$ and $q_N$ as quantities approximately equivalent to the energies of the attenuated LIR and MIR photons originated from the high temperature tissue and the normal temperature tissue respectively, wherein $\theta$ and $\phi$ are respectively the parameters of the high temperature and the normal temperature of the body region; and establishing a cost function, $f$, for the quantitative analysis: C and D are smoothness constraints, $q_{N_0}$ represents an initial state of the $q_N$, and $\lambda$ is the Lagrange multiplier.

2. The quantitative analysis method as claimed in claim 1 further comprising steps of:

deriving evolution equations; and estimating an optimal $q_H$ map, wherein the $q_H$ map is an energy distribution of the high temperature tissue.

3. The quantitative analysis method as claimed in claim 2, wherein the evolution equations for $q_N$ and $q_H$ are:

$$q_N^{n+1} = \frac{\{[\alpha_H \overline{q}_H^n + (X_L\cos\theta + X_M\sin\theta)]\cos(\theta - \phi)\} - [\alpha_N \overline{q}_N^n + (X_L\cos\phi + X_M\sin\phi) + \lambda q_{N0}](1 + \alpha_H)}{\cos^2(\theta - \phi) - (1 + \alpha_H)(1 + \alpha_N + \lambda)}$$

$$q_H^{n+1} = \frac{\{\alpha_N \overline{q}_N^n + (X_L\cos\phi + X_M\sin\phi) + \lambda q_{N0}]\cos(\theta - \phi)\} - [\alpha_H \overline{q}_H^n + (X_L\cos\theta + X_M\sin\theta)](1 + \alpha_N + \lambda)}{\cos^2(\theta - \phi) - (1 + \alpha_H)(1 + \alpha_N + \lambda)}.$$

4. The method as claimed in claim 2, wherein the $q_H$ map is thresholded in such a way that all values of the cost function smaller than 0.001 are set to 0.

5. The quantitative analysis method as claimed in claim 1, wherein the body region is a part of body with tumors and its surrounding areas which reveals heat pattern on the body skin, and the two effective volumes $k_N$ and $k_H$, which take into account the energy attenuation during the propagation from the IR photon generation site to the body surface, are not equivalent to the actual volume.

6. The quantitative analysis method as claimed in claim 1 further being a dual-spectrum heat pattern separation (DS-HPS) algorithm.

7. The quantitative analysis method as claimed in claim 1, wherein the LIR and MIR images further are single-time or time-series images treated with chemotherapy.

8. A method for a dual-spectrum heat pattern separation (DS-BPS), comprising:

establishing a cost function of the dual-spectrum heat pattern separation algorithm based on a vector of a corresponding point pair in a long Infra-red (LIR) image and a medium Infra-red (MIR) image; and using evolution equations to estimate a $q_H$ map from the cost function, wherein the $q_H$ map is an energy distribution map to show the emitted energy from the high temperature tissue.

9. The method as claimed in claim 8, wherein an area and the $q_H$ value in the high temperature tissue are used to analyze quantitatively effectiveness of chemotherapy and further to detect where the tumor is.

10. The method as claimed in claim 8, wherein the LIR and the MIR images are single-time or time-series images treated with chemotherapy.

11. The quantitative analysis approach as claimed in claim 8, wherein the vector X is an energy reading vector approximated by the following equation (I):

$$X = \begin{bmatrix} x_L \\ x_M \end{bmatrix} = \begin{bmatrix} L_H & L_N \\ M_H & M_N \end{bmatrix} \begin{bmatrix} k_H \\ k_N \end{bmatrix}, \quad (I)$$

where $X=(x_L,x_M)$ being the energy reading vector of a corresponding point pair in the LIR and the MIR images, $(L_N, M_N)$ respectively represents the LIR and MIR energy emitted from an unit volume of normal temperature tissue, $(L_H, M_H)$ represents the LIR and MIR energy emitted from an unit volume of a high temperature tissue, and $k_H$ and $k_N$ are two effective volumes of the high temperature tissue and the normal temperature tissue respectively.

12. The method as claimed in claim 8, wherein the energy reading vector further is represented as:

$$X = \begin{bmatrix} x_L \\ x_M \end{bmatrix} = \begin{bmatrix} \cos\theta & \cos\phi \\ \sin\theta & \sin\phi \end{bmatrix} \begin{bmatrix} q_H \\ q_N \end{bmatrix},$$

by letting $L_H=A_H \cos\theta$, $M_H=A_H \sin\theta$, $L_N=A_N \cos\phi$, $M_N=A_N \sin\phi$, $q_H=A_H k_H$ and $q_N=A_N k_N$ and by considering $q_H$ and $q_N$ as quantities approximately equivalent to the energies of the attenuated LIR and MIR photons originated from the high temperature tissue and the normal temperature tissue, and $\theta$ and $\phi$ are respectively the parameters of the high temperature and the normal temperature.

13. The method as claimed in claim 12 being formulated as a blind source separation (BSS) algorithm.

14. The method as claimed in claim 12 further comprising a step of deriving evolution equations for the $q_N$ and the $q_H$.

15. The method as claimed in claim 8 further comprising a step of using a spatiotemporal registration algorithm to register the LIR and the MIR images.

16. A method for establishing a dual-spectrum heat pattern separation (DS-HPS) algorithm to distinguish a high temperature tissue from a normal temperature tissue in a body region, comprising a step of formulating a cost function of the DS-HPS algorithm by assuming that parameters $\phi$ and $q_N$ change slowly in the normal temperature tissue, wherein the cost function, $f$, for the quantitative analysis is:

$f=A+B+C+D+\lambda[q_N-q_{N0}]^2$, wherein $A=[X_L-(\cos\theta \cdot q_H+\cos\phi \cdot q_N)]^2$, $B=[X_M-(\sin\theta \cdot q_H+\sin\phi \cdot q_N)]^2$, $$C = \alpha_H^2\left[\left(\frac{\partial q_H}{\partial x}\right)^2 + \left(\frac{\partial q_H}{\partial y}\right)^2\right],$$

$$D = \alpha_N^2\left[\left(\frac{\partial q_N}{\partial x}\right)^2 + \left(\frac{\partial q_N}{\partial y}\right)^2\right],$$

$f=A+B+C+D+\lambda[q_N-q_{N0}]^2$, wherein $A=[X_L-(\cos\theta \cdot q_H+\cos\phi \cdot q_N)]^2$, $B=[X_M-(\sin\theta \cdot q_H+\sin\phi \cdot q_N)]^2$ $$C = \alpha_H^2\left[\left(\frac{\partial q_H}{\partial x}\right)^2 + \left(\frac{\partial q_H}{\partial y}\right)^2\right],$$

$$D = \alpha_H^2\left[\left(\frac{\partial q_N}{\partial x}\right)^2 + \left(\frac{\partial q_N}{\partial y}\right)^2\right],$$

the parameter $\phi$ is the normal temperature parameter of the body region, the $q_H$ and $q_N$ is the energies for attenuated LIR and MIR photons originated from the high and normal temperature tissue, respectively, $\theta$ and $\phi$ are respectively the parameters of the high temperature and the normal temperature of the body region, $(x_L, x_M)$ is the energy reading vector of a corresponding point pair in the LIR and MIR images, C and D are smoothness constraints, $q_{N_0}$ represents an initial state of the $q_N$, and $\lambda$ is the Lagrange multiplier.

17. The method as claimed in claim 16, wherein the body region comprises a part of body with tumors and its surrounding areas which reveals heat pattern on the body skin.

18. The method as claimed in claim 16 further comprising a step of estimating a $q_H$ map from the cost function.

19. The method as claimed in claim 16, wherein the $q_H$ map is an energy distribution map to show the emitted energies from the high temperature tissue.

* * * * *